(12) United States Patent
Punyani et al.

(10) Patent No.: US 10,980,723 B2
(45) Date of Patent: Apr. 20, 2021

(54) NON-AQUEOUS COMPOSITION FOR HAIR FRIZZ REDUCTION

(71) Applicant: The Procter & Gamble Company, Cincinnati, OH (US)

(72) Inventors: Supriya Punyani, Singapore (SG); Kristine Suzanne So Yu, Singapore (SG); Ioannis Constantine Constantinides, Wyoming, OH (US); Jennifer Mary Marsh, Deerfield Township, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 10 days.

(21) Appl. No.: 15/949,555

(22) Filed: Apr. 10, 2018

(65) Prior Publication Data

US 2018/0289603 A1 Oct. 11, 2018

Related U.S. Application Data

(60) Provisional application No. 62/483,564, filed on Apr. 10, 2017.

(51) Int. Cl.
| | | |
|---|---|---|
| *A61K 8/34* | (2006.01) | |
| *A61K 8/365* | (2006.01) | |
| *A61K 8/37* | (2006.01) | |
| *A61K 8/36* | (2006.01) | |
| *A61K 8/89* | (2006.01) | |
| *A61K 8/92* | (2006.01) | |
| *A61K 8/58* | (2006.01) | |
| *A61K 8/42* | (2006.01) | |
| *A61K 8/31* | (2006.01) | |
| *A61K 8/81* | (2006.01) | |
| *A61K 8/892* | (2006.01) | |
| *A61Q 5/06* | (2006.01) | |
| *A61Q 5/12* | (2006.01) | |
| *A61Q 5/00* | (2006.01) | |

(52) U.S. Cl.
CPC .............. *A61K 8/342* (2013.01); *A61K 8/31* (2013.01); *A61K 8/345* (2013.01); *A61K 8/361* (2013.01); *A61K 8/365* (2013.01); *A61K 8/37* (2013.01); *A61K 8/42* (2013.01); *A61K 8/58* (2013.01); *A61K 8/585* (2013.01); *A61K 8/8158* (2013.01); *A61K 8/89* (2013.01); *A61K 8/892* (2013.01); *A61K 8/922* (2013.01); *A61Q 5/06* (2013.01); *A61Q 5/12* (2013.01); *A61K 2800/31* (2013.01); *A61Q 5/006* (2013.01)

(58) Field of Classification Search
None
See application file for complete search history.

(56) References Cited

U.S. PATENT DOCUMENTS

| | | | |
|---|---|---|---|
| 2,392,314 A | 1/1946 | Dalton | |
| 4,329,097 A | 5/1982 | Steele et al. | |
| 4,496,536 A | 1/1985 | Moller et al. | |
| 4,536,399 A | 8/1985 | Flynn et al. | |
| 4,678,475 A | 7/1987 | Hoshowski et al. | |
| 5,102,655 A | 4/1992 | Yoshihara et al. | |
| 5,384,114 A | 1/1995 | Dowell et al. | |
| 5,565,193 A * | 10/1996 | Midha | A61Q 5/06 424/70.12 |
| 5,587,155 A | 12/1996 | Ochiai et al. | |
| 5,688,495 A | 11/1997 | Rosen et al. | |
| 6,001,340 A | 12/1999 | Rosen et al. | |
| 6,048,520 A * | 4/2000 | Hoshowski | A61K 8/11 424/70.17 |
| 6,156,299 A | 12/2000 | Rosen et al. | |
| 6,294,186 B1 | 9/2001 | Beerse et al. | |
| 6,390,101 B1 * | 5/2002 | Alexander | A45D 2/002 132/112 |
| 6,495,498 B2 | 12/2002 | Niemiec et al. | |
| 6,726,312 B1 * | 4/2004 | Fujimura | B41J 2/14233 347/47 |
| 6,858,202 B2 | 2/2005 | Niemiec et al. | |

(Continued)

FOREIGN PATENT DOCUMENTS

| | | | |
|---|---|---|---|
| DE | 19536423 A1 | 4/1996 | |
| DE | 1020011089357 A1 | 8/2012 | |
| EP | 0661965 B1 | 6/1999 | |
| EP | 1787680 A2 | 5/2007 | |
| EP | 1326577 B1 | 10/2008 | |
| EP | 2036536 A1 | 3/2009 | |
| EP | 2392314 A1 | 12/2011 | |
| FR | 2930141 A1 * | 10/2009 | .............. A61K 8/27 |
| FR | 2931659 B1 | 3/2011 | |
| FR | 2968946 B1 | 4/2013 | |

(Continued)

OTHER PUBLICATIONS

All final and non-final office actions for U.S. Appl. No. 15/473,832 (P&G Case 14271).

(Continued)

*Primary Examiner* — Aradhana Sasan
(74) *Attorney, Agent, or Firm* — Linda M. Sivik

(57) ABSTRACT

A non-aqueous hair leave-on composition directed to an aqueous hair leave-on composition for hair frizz reduction comprising from about 0.15% to about 12.0% of a moisture control material or mixture of moisture control materials wherein the moisture control material is selected from one or more of the Class II groups a, b, c, d, e, f and g and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4; and wherein, the non-aqueous carrier is selected from a group consisting of
a) hydrocarbons
b) silicone fluid
c) non-hydrocarbons volatile organic solvents or mixtures thereof.

33 Claims, No Drawings

(56) References Cited

U.S. PATENT DOCUMENTS

| | | |
|---|---|---|
| 6,908,889 B2 | 6/2005 | Niemiec et al. |
| 7,303,744 B2 | 12/2007 | Wells |
| 7,527,654 B2 | 5/2009 | Plos |
| 8,173,144 B2 | 5/2012 | Bernard |
| 8,349,301 B2 | 1/2013 | Wells |
| 8,349,302 B2 | 1/2013 | Johnson |
| 8,361,448 B2 | 1/2013 | Johnson |
| 8,361,449 B2 | 1/2013 | Wells |
| 8,361,450 B2 | 1/2013 | Johnson |
| 8,367,048 B2 | 2/2013 | Wells |
| 8,470,305 B2 | 6/2013 | Johnson |
| 8,512,686 B2 | 8/2013 | Morioka |
| 8,968,712 B2 | 3/2015 | Tanaka |
| 9,095,528 B2 | 8/2015 | Desenne et al. |
| 9,216,146 B2 | 12/2015 | Tanaka |
| 9,259,070 B2 | 2/2016 | Fischer et al. |
| 9,265,321 B2 | 2/2016 | Fischer et al. |
| 9,271,908 B2 | 3/2016 | Allef et al. |
| 9,877,909 B2 | 1/2018 | Cetti et al. |
| 10,111,815 B2 | 10/2018 | Marsh et al. |
| 10,258,555 B2 | 4/2019 | Punyani |
| 10,406,094 B2 | 9/2019 | Punyani |
| 10,561,591 B2 | 2/2020 | Punyani |
| 10,632,054 B2 | 4/2020 | Punyani |
| 10,660,835 B2 | 5/2020 | Punyani |
| 2002/0010228 A1 | 1/2002 | Simendinger |
| 2003/0022936 A1 | 1/2003 | Milbradt et al. |
| 2003/0031643 A1* | 2/2003 | L'alloret ............... A61K 8/06 424/70.16 |
| 2003/0143173 A1 | 7/2003 | Buck |
| 2003/0170195 A1 | 9/2003 | Houze et al. |
| 2003/0199584 A1 | 10/2003 | Ahluwalia |
| 2003/0215405 A1 | 11/2003 | Parker et al. |
| 2003/0223952 A1 | 12/2003 | Wells et al. |
| 2004/0120911 A1 | 6/2004 | Shah et al. |
| 2004/0180016 A1 | 9/2004 | Buck |
| 2004/0251198 A1 | 12/2004 | Lord |
| 2005/0136015 A1* | 6/2005 | McKie ............... A61K 8/368 424/70.1 |
| 2005/0143268 A1 | 6/2005 | Midha et al. |
| 2005/0169869 A1 | 8/2005 | Laurent et al. |
| 2005/0175567 A1 | 8/2005 | Khoshdel et al. |
| 2005/0196369 A1 | 9/2005 | Ueyama et al. |
| 2005/0266034 A1 | 12/2005 | Muller et al. |
| 2006/0078523 A1 | 4/2006 | Vic |
| 2006/0127337 A1 | 6/2006 | Radisson |
| 2006/0165636 A1 | 7/2006 | Hasebe et al. |
| 2006/0204466 A1 | 9/2006 | Littau et al. |
| 2006/0286059 A1 | 12/2006 | Yang et al. |
| 2007/0014748 A1 | 1/2007 | Bernard |
| 2007/0104667 A1 | 5/2007 | Mondet et al. |
| 2007/0110694 A1* | 5/2007 | Hoffmann ............ A61K 8/37 424/70.12 |
| 2007/0149423 A1 | 6/2007 | Warr et al. |
| 2007/0261179 A1 | 11/2007 | Dorkel et al. |
| 2008/0070875 A1 | 3/2008 | Majewski |
| 2008/0131389 A1 | 6/2008 | Shibuya |
| 2008/0138438 A1 | 6/2008 | Taylor et al. |
| 2008/0194454 A1 | 8/2008 | Morgan et al. |
| 2009/0104136 A1 | 4/2009 | Anderson |
| 2009/0169502 A1 | 7/2009 | Quadir |
| 2009/0324531 A1 | 12/2009 | Okada et al. |
| 2010/0297051 A1 | 11/2010 | Feuillette |
| 2010/0300472 A1 | 12/2010 | Malle et al. |
| 2010/0330007 A1 | 12/2010 | Spindler et al. |
| 2011/0003016 A1 | 1/2011 | Burry et al. |
| 2011/0226275 A1 | 9/2011 | Fischer et al. |
| 2011/0256249 A1 | 10/2011 | Campbell |
| 2011/0269658 A1 | 11/2011 | Dihora et al. |
| 2011/0274642 A1 | 11/2011 | Yamaki |
| 2012/0070398 A1 | 3/2012 | Nagano et al. |
| 2012/0093751 A1 | 4/2012 | Nagano et al. |
| 2012/0308506 A1 | 12/2012 | Oku |
| 2013/0064908 A1 | 3/2013 | Noh |
| 2013/0125915 A1 | 5/2013 | Nagase et al. |
| 2013/0164390 A1 | 6/2013 | Richards et al. |
| 2013/0167862 A1 | 7/2013 | Lopez et al. |
| 2013/0259817 A1 | 10/2013 | Uehara et al. |
| 2013/0259819 A1 | 10/2013 | Uehara et al. |
| 2013/0306095 A1 | 11/2013 | Syed |
| 2013/0309190 A1 | 11/2013 | Dimotakis et al. |
| 2014/0079660 A1 | 3/2014 | Doi |
| 2014/0154197 A1 | 6/2014 | Swaile et al. |
| 2014/0179645 A1 | 6/2014 | Arndt |
| 2014/0335042 A1 | 11/2014 | Peffly |
| 2015/0174052 A1 | 6/2015 | Mette et al. |
| 2015/0313816 A1 | 11/2015 | Daubresse |
| 2015/0313832 A1 | 11/2015 | Hilvert et al. |
| 2015/0359716 A1 | 12/2015 | Marsh et al. |
| 2015/0374609 A1 | 12/2015 | Cetti et al. |
| 2016/0015608 A1 | 1/2016 | Marsh et al. |
| 2016/0022558 A1 | 1/2016 | Kunin et al. |
| 2016/0158128 A1 | 6/2016 | Marsh et al. |
| 2016/0158135 A1 | 6/2016 | Marsh et al. |
| 2016/0175209 A1 | 6/2016 | Walker et al. |
| 2016/0228342 A1 | 8/2016 | Rose |
| 2016/0287494 A1 | 10/2016 | Punyani et al. |
| 2016/0287495 A1 | 10/2016 | Punyani et al. |
| 2017/0157008 A1 | 6/2017 | Punyani et al. |
| 2017/0157009 A1 | 6/2017 | Punyani et al. |
| 2017/0157011 A1 | 6/2017 | Punyani et al. |
| 2017/0216172 A1 | 8/2017 | Carballada et al. |
| 2017/0281523 A1 | 10/2017 | Punyani et al. |
| 2017/0290755 A1 | 10/2017 | Soh et al. |
| 2018/0289605 A1 | 10/2018 | Punyani et al. |

FOREIGN PATENT DOCUMENTS

| | | |
|---|---|---|
| GB | 816750 | 7/1959 |
| JP | S63156711 A | 6/1988 |
| JP | H06256137 A | 9/1994 |
| JP | 3009959 B2 | 2/2000 |
| JP | 3026213 B2 | 3/2000 |
| JP | 2001122737 A | 5/2001 |
| JP | 2005145883 A | 6/2005 |
| JP | 2005194261 A | 7/2005 |
| JP | 3843051 B2 | 11/2006 |
| JP | 2006298916 A | 11/2006 |
| JP | 2007070469 A | 3/2007 |
| JP | 4329097 B2 | 9/2009 |
| JP | 4452523 B2 | 4/2010 |
| JP | 4625357 B2 | 2/2011 |
| JP | 4679893 B2 | 5/2011 |
| JP | 4883261 B2 | 2/2012 |
| JP | 5086539 B2 | 11/2012 |
| JP | 5280873 B2 | 5/2013 |
| JP | 5228338 B2 | 7/2013 |
| JP | 2014097931 A | 5/2014 |
| JP | 5779399 B2 | 9/2015 |
| WO | WO200128338 A2 | 4/2001 |
| WO | WO200128339 A2 | 4/2001 |
| WO | WO2011074134 A1 | 6/2011 |
| WO | WO2012131848 A1 | 10/2012 |
| WO | WO2014002668 A2 | 1/2014 |
| WO | WO2014100970 A1 | 7/2014 |
| WO | WO2015200778 A1 | 12/2015 |

OTHER PUBLICATIONS

Benvenuti, http://www.futurederm.com/what-is-the-best-oil-for-your-hair-argan-oil-vs-pequi-oil-review/, 2011, downloaded Dec. 30, 2018.

Dow Corning: "Get on the FastTrack to Dry with silicones from Dow Corning", Nov. 19, 2015.

Dow Corning: "Leave-In Conditioner: Fast Dry", Dec. 9, 2015.

Dow Corning: "Revivel Hair Repair Cream: Ideal to Repair Heat Damaged Hair", Jan. 21, 2015.

Dow Corning: "Rinse-Off Conditioner: Fast Dry", Dec. 9, 2015.

Knothe et al., J. Am Oil Chem Soc., 86, pp. 843-856 (2009).

LotionCrafter (https://lotioncrafter.com/reference/tech_data_lc995.pdf) available on archieve.org on Nov. 23, 2015, pp. 1-2 (2015).

Merriam-Webster Dictionary, obtained online at https://www.merriam-webster.com/dictionary/pH, downloaded on Jun. 29, 2018, pp. 1-14 (2018).

(56) References Cited

OTHER PUBLICATIONS

Naturally.com, "Salicylic Acid Shampoo for Curly Hair", pp. 1-3, 2011.
Olivella, M., et al., "Salicylic acid permeation: A comparative study with different vehicles and membranes", Biocell, pp. 321-324 Year: 2006).
PCT International Search Report and Written Opinion for PCT/US2017/024965 dated Jun. 13, 2017.
Watson, "5 Hair Conditioners You Can Make at Home", retrieved from on-line website: www.wisebread.com, pp. 1-11, 2011.
"De-Frizz Leave-In Treatment", Quality Collor Cosmeticos, May 1, 2014, Mintel.
"Infusion 23 (Colour) Ologie Leave-In Treatment", Procter & Gamble, Feb. 1, 2007, Mintel.
All Final and Non-Final Office Actions for U.S. Appl. No. 14/677,578, P&G Case 13769.
All Final and Non-Final Office Actions for U.S. Appl. No. 14/677,636, P&G Case 13770.
All Final and Non-Final Office Actions for U.S. Appl. No. 14/742,136, P&G Case 13355M.
All Final and Non-Final Office Actions for U.S. Appl. No. 14/742,145, P&G Case 13356M.
All Final and Non-Final Office Actions for U.S. Appl. No. 14/755,567, P&G Case 13461M.
All Final and Non-Final Office Actions for U.S. Appl. No. 14/959,234, P&G Case 13640M.
All Final and Non-Final Office Actions for U.S. Appl. No. 14/959,243, P&G Case 13641M.
All Final and Non-Final Office Actions for U.S. Appl. No. 15/093,075, P&G Case AA1008.
All Final and Non-Final Office Actions for U.S. Appl. No. 15/367,356, P&G Case 14116.
All Final and Non-Final Office Actions for U.S. Appl. No. 15/367,363, P&G Case 14117.
All Final and Non-Final Office Actions for U.S. Appl. No. 15/367,369, P&G Case 14118.
All Final and Non-Final Office Actions for U.S. Appl. No. 15/949,539, P&G Case 14768.
Anonymous: "Spotlight on Apricot Oil, Black Girl with Long Hair", Apr. 5, 2013, Retrieved from the internet: URL: http://blackgirllonghair.com/2013/04/spotlight-on-apricot-oil/, Retrieved Jun. 2, 2016.
John Frieda Frizzease conditioner product (John Frieda, Frizzease smooth start conditioner—https://www.johnfrieda.com/en-UK/products/frizz-ease/smooth-start-conditioner.html, last visit date: Jan. 17, 2018 (year 2018).
Khan, H., "5 ways to straighten your hair without heat", Hair Beauty Tips, Jul. 12, 2013, pp. 1-4.
Medline Plus "Aging changes in hair and nails", US National Library of Medicine, Oct. 27, 2014, pp. 1-3.
PCT International Search Report and Written Opinion for PCT/US2015/036192 dated Mar. 21, 2016.
PCT International Search Report and Written Opinion for PCT/US2015/036195 dated Dec. 16, 2015.
PCT International Search Report and Written Opinion for PCT/US2016/025827 dated Jun. 24, 2016.
PCT International Search Report and Written Opinion for PCT/US2016/064604 dated Apr. 10, 2017.
PCT International Search Report and Written Opinion for PCT/US2016/064606 dated Apr. 12, 2017.
PCT Invitation to Pay Additional Fees and, Where Applicable, Protest Fee for PCT/US2015/036192 dated Jan. 4, 2016.
PCT Invitation to Pay Additional Fees and, Where Applicable, Protest Fee for PCT/US2015/036195, dated Oct. 7, 2015.
PCT Invitation to Pay Additional Fees and, Where Applicable, Protest Fee for PCT/US2015/063888 dated Mar. 9, 2016.
PCT Invitation to Pay Additional Fees and, Where Applicable, Protest Fee for PCT/US2015/063893, dated Feb. 8, 2016.
PCT Invitation to Pay Additional Fees and, Where Applicable, Protest Fee for PCT/US2015/064608 dated Feb. 20, 2017, 9 pages.
PCT Invitation to Pay Additional Fees and, Where Applicable, Protest Fee for PCT/US2016/064604 dated Feb. 15, 2017, 10 pages.
PCT Invitation to Pay Additional Fees and, Where Applicable, Protest Fee for PCT/US2016/064606 dated Feb. 20, 2017, 14 pages.
Retrieved from internet: http://cosmetics.specialchem.com/inci/hydroxyethyl-urea, last visit May 10, 2017.
U.S. Appl. No. 15/949,539, filed Apr. 10, 2018, Punyani et al.

* cited by examiner

NON-AQUEOUS COMPOSITION FOR HAIR FRIZZ REDUCTION

FIELD OF THE INVENTION

The present invention relates to a non-aqueous leave-on composition comprising one or more materials useful for treating hair frizz.

BACKGROUND OF THE INVENTION

Hair frizz is described by consumers as the appearance of unruly fibers at the top of the scalp and tips of hair as well as an increased volume through the bulk of the hair. Generally they see this frizz on days the level of moisture in the air is high. The appearance of frizz is undesired and it is often associated with a loss of shine and smoothness, which are associated with a perception of poor hair health. The common accepted mechanism causing fizz in high humid environments is that at high humidity water penetrates into hair and changes the chemical bonding interactions inside the hair. During styling, the consumer will create a 'wet set' where hair is blow dried or flat ironed to create the desired shape. During drying, water is evaporated from hair and hydrogen bonds (and other bonding interactions) are formed between the protein chains holding the style in place. As moisture diffuses into hair the hydrogen bonds (and other bonding interactions) are broken and hair returns back to its natural shape. For consumers who straighten their hair by blow drying or flat ironing, this return to a curled style is associated with a loss of alignment and increased volume. In addition, at high moisture levels in hair the fiber diameter increases which also increases the overall volume of hair.

The typical strategy to prevent frizz is to formulate leave-on or rinse-off products with surface-depositing materials such as silicone, oils, conditioning silicone etc. which make hair more hydrophobic and decrease inter-fiber interactions. At high levels these materials can also provide increased cohesive forces holding fibers together to prevent frizz from occurring. With these materials depositing on the hair surface a greasy look and feel is typically experienced, which is an undesired trade-off of frizz reduction.

Consequently, a need exists for hair products that are effective in controlling frizz and at the same time delight consumers by providing hair that do not have sticky or greasy feel. This can be achieved by using compositions containing Moisture Control Materials which penetrate hair fibers and reduce the amount of moisture absorbed by hair at high humidity. Traditional water-based leave-on and rinse-off products may be utilized to achieve that Non-aqueous chassis containing moisture control materials may provide higher smoother feel benefit on first leave on application than aqueous chassis. The inventors surprisingly found that many consumers find the in-use experience of anhydrous products more delightful than the experience achieved by aqueous products. We also found that, at high content of Moisture Control Material in an aqueous composition may occasionally show phase instability in comparison to non-aqueous composition. Thus, a need exists for the development of non-aqueous anti-frizz products that enable stable forms at any concentration of the Moisture Control Materials and at the same time provide a more immediate benefit and a delightful experience for the consumers.

SUMMARY OF THE INVENTION

The present invention is directed to a non-aqueous hair leave-on composition for hair frizz reduction comprising:
from about 0.15% to about 12.0% of a moisture control material or mixture of moisture control materials wherein the moisture control material is selected from one or more of the following class:

Class II having the structure selected from:
A)

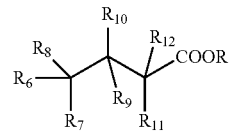

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

B)

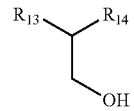

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;

C) alcohol comprising an unsaturated double bond in the C2 position.

D) an alkyl-substituted glycol wherein the structure of such alkyl substituted glycol contains less than 20 carbon atoms;

E) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

F)

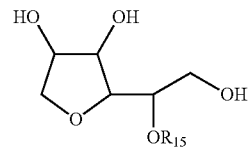

wherein $R_{15}$ could be hydrogen, alkyl, alkenyl, phenyl group and wherein the structure of the $R_{13}$ group contain less than 20 carbon atoms;

G) a fatty acid ester containing from 15-40 total carbon atoms and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4; and wherein, the non-aqueous carrier is selected from a group consisting of
a) hydrocarbons
b) silicone fluid
c) non-hydrocarbons volatile organic solvents or mixtures thereof.

Without being bound by theory, the materials in the non-aqueous leave-on treatment composition of the present invention provide excellent frizz performance without negatively affecting hair feel. These materials prevent water uptake into hair under high humidity conditions, reducing the negative impact of frizz. By providing frizz benefits by penetrating the hair fiber as opposed to depositing on the hair surface, the frizz benefit is not associated by negative hair feel, which is typically observed with current commercial anti-frizz products. These and additional features provided by the embodiments of the present invention will be more fully understood in view of the following detailed description.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

"Non-Aqueous Composition"

The composition of the present invention is a non-aqueous composition. Non-aqueous composition herein means that the composition is substantially free of water. In the present invention, "the composition being substantially free of water" means that: the composition is free of water; or, if the composition contains water, the level of water is very low. In the present invention, the level of water, if included, 2% or less, preferably 0.5% or less, more preferably 0.3% or less, still more preferably 0.1% or less, even more preferably 0% by weight of the composition.

The mechanism of action for frizz generation involves moisture from the environment being absorbed by hair and occupying hydrogen bonding sites within hair, including those on the peptide backbone and also associated with acidic and basic side chains of amino acid residues such as lysine, arginine and glutamic acid. This internal water replaces hydrogen bonds that had been created during styling that hold hair in a desired configuration. As a consequence, hair returns to its natural shape which typically leads to unwanted wave, loss of alignment and frizz. In addition, uptake of water by these hydrogen bonding sites swells the hair fiber causing style expansion, which is another indicator of frizz. Without being bound by theory, the materials in the compositions of the current invention replace water at the hydrogen bond sites inside hair and prevent water uptake. Reduction of water inside hair leads to a reduction in the appearance of frizz under high humidity conditions. Because the mechanism of action is related to the space inside the hair fibers, there are no feel negatives, such as, for example, greasy or oily feel associated with the benefit. The reduction in water uptake is measured using Dynamic Vapor Sorption (DVS) method, which measures a weight increase of hair equilibrated at 0% Relative Humidity (RH) versus 90% RH. Significant frizz benefit is measured on hair treated by materials that caused a reduction in water uptake of higher than 5% versus control hair that is not treated with such materials. The treatment involved the application of a 2% w/w solution of the materials in a mixture of dimethiconol/dimethicone and cyclopentasiloxane/isododecane.

Preferred materials include salicylic acid, 2,3-dihydroxybenzoic acid, 2,6-dihydroxybenzoic acid, 3-aminobenzoic acid, gallic acid, ethyl gallate, 5-chlorosalicylic acid, trans-ferulic acid, p-coumaric acid, ricinoleic acid, isovaleric acid, isobutyric acid, 2-hexyl-1-decanol, phytol and sorbitan caprylate. These materials are chosen from Molecular Class I and/or Molecular Class II or can also be used in combination to increase the size of the benefit.

In an embodiment of the present invention, the concentration of the Moisture Control Material or the concentration of the mixture of Moisture Control Material in a hair non-aqueous leave-on composition is from about 0.15% to about 12%, in an embodiment from about 0.2% to about 5%, in a further embodiment from about 0.5% to about 4%, and in yet a further embodiment from about 1.0% to about 3.0%.

Molecular Class I: Polar, Acidic Compounds with the Following Properties:

Protein Binding (PB)>20 AND Molecular Volume (Mol. Vol). <500 AND log P<3 AND Hydrogen-binding (H-binding) >10 AND pKa <5.0, wherein PB is % protein binding, Mol. Vol is molecular volume (in $Å^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name (1% wt/vol) | PB | Mol. Vol. | log P | pKa | H-bond $(MPa^{1/2})$ | % Water Reduction |
|---|---|---|---|---|---|---|
| 2,4-Dihydroxybenzoic acid | 28 | 324 | 1.5 | 3.2 | 23 | 30 |
| 3-Hydroxybenzoic Acid | 38 | 314 | 1.6 | 4.3 | 20 | 20 |
| Gallic acid | 23 | 337 | 0.9 | 4.4 | 23 | 15 |
| 3-Aminobenzoic acid | 41 | 326 | 0.9 | 3.6 | 16 | 12 |
| 4-Aminobenzoic acid | 42 | 323 | 0.9 | 3.5 | 16 | 12 |
| 2,5-Dihydroxybenzoic acid | 31 | 329 | 1.6 | 2.9 | 23 | 27 |
| 3,4-Dihydroxybenzoic acid | 27 | 327 | 0.9 | 4.4 | 23 | 20 |
| 3,5-Dihydroxybenzoic acid | 27 | 327 | 0.9 | 4.1 | 23 | 15 |
| 2,6-Dihydroxybenzoic acid | 37 | 326 | 1.6 | 2.1 | 23 | 35 |
| 5-Chlorosalicylic acid | 56 | 361 | 2.3 | 3.0 | 21 | 28 |
| Salicylic acid | 44 | 320 | 2.1 | 3.1 | 20 | 18 |
| Trans-Ferulic Acid | 50 | 451 | 1.5 | 4.5 | 19 | 6 |
| p-Coumaric acid | 46 | 391 | 1.6 | 4.5 | 20 | 8.8 |
| 4-Hydroxybenzenesulphonic acid | 55 | 271 | 1.5 | 2.7 | 22 | 26 |
| 3-Chloro-4-hydroxybenzoic acid | 49 | 356 | 2.1 | 4.1 | 20 | 11 |
| 3,5-Dichloro-4-hydroxybenzoic acid | 51 | 397 | 2.8 | 3.8 | 20 | 15 |
| 2,5 Dihydroxyterephthalic acid | 20 | 375 | 1.1 | 2.1 | 22 | 18 |
| 3-Aminophenol | 45 | 284 | 0.6 | 4 | 17 | 14 |
| 3-Hydroxyanilinium chloride | 32 | 280 | 0.6 | 4 | 17 | 16 |
| 2-Aminophenol | 49 | 288 | 1.0 | 4 | 17 | 14 |
| 4-Aminophenol | 39 | 284 | 0.6 | 4 | 17 | 10 |
| N-4-Hydroxyphenylglycine | 37 | 388 | 1.3 | 3 | 13 | 15 | b) Molecular Class II: Weakly polar to non-polar, weakly to non-acidic compounds that have the following properties: PB>10 AND Mol. Vol. <1500 AND log P >0.5 AND pKa ≥5 AND H-binding >4, wherein PB is % protein binding, Mol. Vol is molecular volume (in $Å^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name | PB | Mol. Vol. | logP | pKa | H-bond $(MPa^{1/2})$ | % water reduction |
|---|---|---|---|---|---|---|
| 2-Hydroxyethyl salicylate | 45 | 419 | 1.5 | 8.3 | 19.1 | 10 |
| Ethyl gallate | 43 | 431 | 1.4 | 8.7 | 22.6 | 17 |
| Oleic Acid | 100 | 832 | 7 | 5 | 6.4 | 14 |
| Ricinoleic acid | 84 | 841 | 5.9 | 5 | 17.8 | 8.8 |
| Isovaleric acid | 29 | 295 | 1.3 | 5 | 9.7 | 15 |
| Isobutyric acid | 15 | 254 | 1 | 5 | 10.4 | 5 |
| 2-Hexyl-1-decanol | 87 | 745 | 6.8 | 15 | 10.1 | 11 |
| Phytol | 100 | 874 | 8.0 | 13 | 9.6 | 14 |
| Sorbitan caprylate | 32 | 695 | 1.3 | 12 | 21.8 | 11 |
| Glyceryl monooleate | 96 | 974 | 6.27 | 12.8 | 16.2 | 5 |
| Isostearyl isostearate | 100 | 1527 | 14.7 | 14 | 4.2 | 11 |
| Ethyl linoleate | 82 | 903 | 7.71 | 7.8 | 5.1 | 8 |
| Isopropyl myristate | 97 | 798 | 6.99 | 8.8 | 5.0 | 12 |
| Octyl salicylate | 82 | 646 | 5.4 | 7.1 | 11.7 | 14 |

A Class I having the structure selected from:

1) Class I having the structure selected from:

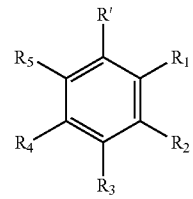

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

2) Class II having the structure selected from:

A)

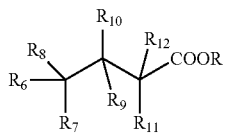

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

B)

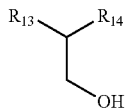

an alcohol wherein $R_{13}$ is an alkyl, alkenyl, straight or branched carbon chains and; and wherein $R_{14}$ is hydrogen, hydroxyl, alkyl, methyl, ethyl and propyl wherein the structure of such alcohol contains less than 20 total carbon atoms;

c) An alcohol comprising an unsaturated double bond in the C2 position. A non limiting example would be phytol.
d) an alkyl-substituted glycol wherein the structure of such alkyl substituted glycol contains less than 20 carbon atoms;
e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;
f)

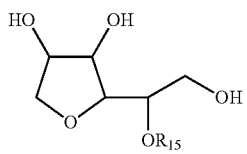

wherein $R_{15}$ could be hydrogen, alkyl, alkenyl, phenyl group and wherein the structure of the $R_{13}$ group contains less than 20 carbon atoms;

g) a fatty acid ester containing from 15-40 total carbon atoms and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4;

pH of Compositions

In an embodiment of the present invention, the table below demonstrates data of the difference of % water reduction of hair treated with leave on composition containing 1% salicylic acid in ethanol:water (50:50) at various values of pH vs control (hair treated with composition of ethanol:water (50:50). As shown in below table, at lower pH, the present invention demonstrates improved performance compared to higher pH.

| Raw Material | Formula Example | | | |
| --- | --- | --- | --- | --- |
| | pH 3 | pH 4.2 | pH 7 | pH 10 |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Water Reduction | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the pH of a composition of the present invention comprising materials from Molecular Class II may be in the range of from about 1 to about 9, in another embodiment a pH of from about 2 to about 8, and in a further embodiment a pH of from about 3 to about 7.

In an embodiment of the present invention, the Moisture control Material is a carboxylic acid ester. In an embodiment, the carboxylic acid ester is based on a fatty acid wherein the molecule of the fatty acid comprises of more than 14 carbon atoms. Non-limiting examples of such esters are isostearyl isostearate, methyl stearate, methyl palmitate, and methyl oleate. In another embodiment of the present invention, the carboxylic acid ester is part of a mixture of materials prepared via the reaction of natural oils using methanol. Non-limiting examples of such mixture is the mixture that is produced by the product of the reaction of refined palm kernel oil with methanol, followed by fractionation via distillation. A commercial product that meets this description is the Heavy Cut Ester CE-1875 (supplied by P&G Chemicals with CAS Number 6772-38-3) containing ingredients such as methyl stearate, methyl palmitate, methyl oleate as major ingredients, as well as methyl laurate, methyl myristate, methyl behenate and other materials as minor ingredients.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Examples

Method of Making Aqueous Leave-on Treatment Compositions

The leave-on treatment compositions are prepared by adding the Moisture Control Materials and perfume, if needed, into a 50:50 ethanol/water carrier and stirred until complete dissolution. The solution pH is adjusted using sodium hydroxide (50% w/w) to a final pH of 4.0-4.2. The Sepigel 305 is then added, if needed, and the solution is mixed using a high-speed-mixer for 2-5 minutes at 1800-2300 rpm until a uniform composition is obtained.

Method of Making Non-Aqueous Leave-on Treatment Compositions

The non-aqueous leave-on treatment compositions are prepared by adding the Moisture Control Materials and perfume, if needed, into a mixture of Dimethiconol/Dimethicone and Cyclopentasiloxane/Isododecane and stirred until complete dissolution. Additionally, propylene glycol is added to aid in dissolution of moisture control materials at high levels of dimethicone. The viscosity of the composition varies from approximately 20 mPa s to 2500 mPa s at 20° C., which primarily depends on the amount of dimethicone added.

Method of Making of Non-Aqueous Leave-on Treatment Composition in a Solid Form

The leave-on treatment composition in solid form is prepared by mixing together two different compositions. A premix and main-mix. A Premix of SAPDMA (stearamidopropyl dimethylamine and phenyl trimethicone are mixed together at ambient conditions. The main mix is prepared wherein addition of all other ingredients together is completed. The main mix is heated to 75-100° C. The premix is then added to the main mix at 75-100° C. temperature, while mixing. And proceeded to be mixed for 5 minutes minimum. The heat is turned off to the batch, allowing to slowly cool while mixing. Batch is then poured into a Teflon mold.

Method of Treating Hair with Aqueous Leave-on Composition

An amount of 0.20 g of each composition of Examples I to IV is applied via syringe and massaged for 30 seconds onto separate natural virgin brown hair switches weighing 2.0 g (dosage 0.10 g of solution per g of hair). The hair is allowed to air dry and then analyzed using the DVS method described above. The experiment is repeated for a dosage of 0.50 g of solution per g of hair. The hair in this case is also assessed by expert graders, as described below, in addition to the DVS analysis.

Method of Treating Hair with Non-Aqueous Leave-on Composition

An amount of 0.20 g of each composition of Examples A to J is applied via syringe and massaged for 30 seconds onto separate natural virgin brown hair switches weighing 2.0 g (dosage 0.10 g of solution per g of hair). The hair is allowed to air dry and then analyzed using the DVS method described above. The hair in this case is also assessed by expert graders, as described below, in addition to the DVS analysis.

DVS Measurement Method

An amount of 25-30 mg of hair with length of approximately 1 cm is weighed and hold for equilibration at 0% Relative Humidity (RH) for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed by the hair treated with composition containing the Moisture Control Material
B=Amount of water absorbed by the hair treated with control composition (only carrier) containing no Moisture Control Material $$\% \text{ Water reduction} = [(B-A) \times 100]/B$$

Hair Switch Frizz Assessment Method

The treated hair switches are kept at high humidity (above 85% RH) for 2 hrs and then ten expert graders are asked to rate each of them in terms of frizz appearance based on a 5 point scale, 5 being the worst frizz and 1 being the best frizz control.

Hair Switch Feel Assessment Method

The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

In-Use Product Feel Assessment on Hair Switch

Ten expert graders are asked to apply formulation on hair and rate each formulation based on a 5 point scale for in-use feel assessment, 5 being the highest (best feel) and 1 being the lowest rating.

Method of Determining Stability of the Compositions

Leave-on compositions are kept at 40° C. at 60% RH to visually assess any precipitation on day 1 and after a week of storage at these conditions.

TABLE 1

Aqueous Leave-on Treatment Formulation:

| Raw Material | Leave-on treatment Control (wt./wt.)% | I (wt./wt.)% | II (wt./wt.)% | III (wt./wt.)% | IV (wt./wt.)% | V (wt./wt.)% | VI (wt./wt.)% | VII (wt./wt.)% |
|---|---|---|---|---|---|---|---|---|
| Distilled Water | QS | QS | QS | QS | QS | QS | QS | QS |
| Ethanol | 50.00 | 50.00 | 50.00 | 50.00 | 50.00 | 50.00 | 50.00 | 50.00 |
| Polyacrylamide & C13-14 Isoparaffin & Laureth-7 (Sepigel 305) | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 |
| 5-Chlorosalicylic acid | 0 | 0 | 2.0 | 0 | 0 | 0 | 2.0 | 2.0 |
| 2,4-Dihydroxybenzoic acid | 0 | 0 | 0 | 2.0 | 0.15 | 0.15 | 0.15 | 0.15 |
| Oleic acid | 0 | 0 | 0 | 0 | 0 | 0.25 | 0 | 0.25 |
| 2-Hexyl-1-decanol | 0 | 0 | 0 | 0 | 0 | 0.25 | 0 | 0.25 |
| Final pH | 4.2 | 4.2 | 4.2 | 4.2 | 4.2 | 4.2 | 4.2 | 4.2 |

TABLE 1-continued

Aqueous Leave-on Treatment Formulation:

| Raw Material | Leave-on treatment Control (wt./wt.)% | I (wt./wt.)% | II (wt./wt.)% | III (wt./wt.)% | IV (wt./wt.)% | V (wt./wt.)% | VI (wt./wt.)% | VII (wt./wt.)% |
|---|---|---|---|---|---|---|---|---|
| % Water Reduction versus Leave-on Treatment Control at dose of 0.10 g of composition for 1.0 g of hair | '— | — | — | — | 4 | 5 | 5 | 7 |
| % Water Reduction versus Leave-on Treatment Control at dose of 0.50 g of composition for 1.0 g of hair. Control is dosed at 0.50 g of composition for 1.0 g of hair | — | 4 | 5 | 5 | 9 | 8 | 10 | 10 |
| Feel Rating Leave-on Treatment Control at dose of 0.10 g of composition for 1.0 g of hair | 1 | 1 | 2 | 2 | 2 | 3 | 2 | 4 |

TABLE 2

Examples of Aqueous Leave on Formulation Treatment Composition (Single variable)

| Raw Material | VIII | IX | X | XI | XII | XIII |
|---|---|---|---|---|---|---|
| Distilled Water | QS | QS | QS | QS | QS | QS |
| Ethanol | 50.0 | 50.0 | 50.0 | 50.0 | 50.0 | 50.0 |
| 5-Chlorosalicylic acid | 1.0 | | | 1.0 | 1.0 | 1.0 |
| 2-Hexyl-1-decanol | | | 5.0 | 5.0 | | 5.0 |
| Isostearyl isostearate | | 2.0 | | | 2.0 | 2.0 |
| Final pH | 4 | 4 | 4 | 4 | 4 | 4 |
| % Water Reduction versus Leave-on Treatment Control at dose of 0.10 g of composition for 1.0 g of hair | 1.3 | 0.7 | 1.0 | 2.0 | 1.4 | 3.0 |
| Feel Rating (on 5 scale point with 5 as highest and 1 as lowest) | 1 | 2 | 2 | 3 | 3 | 4 |

Results:

Formula I to XIII showed % water reduction at high humidity. Higher % water reductions are observed in hair treated with higher doses of leave-on Formulas I-XIII.

The feel assessment results indicate that combinations of
(a) 5-Chlorosalicylic acid and 2-hexyl-1-decanol;
(b) 5-Chlorosalicylic acid and isostearyl isostearate;
(c) 5-Chlorosalicylic acid and 2-hexyl-1-decanol and isostearyl isostearate provide, not only water absorption reduction (resulting in frizz benefit), but also tactile feel benefit. This is shown by the feel comparisons of (a) Example XI versus Examples VIII and IX, (b) Example XII versus Examples VIII and X, and (c) Example XIII versus Examples VIII, IX and X.

Additional Evaluations

Additional leave-on treatment compositions are prepared (Tables 1 and 2) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, and greasy feel, based on a 5 point scale, 5 being the highest and 1 being the lowest rating.

TABLE 3

Aqueous compositions containing Class I Moisture Control Materials

| Raw Material | Control | XIV | XV | XVI | XVII | XVIII |
|---|---|---|---|---|---|---|
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| 5-Chlorosalicylic acid | 0% | 1% | 0% | 0% | 0% | 0% |
| Salicylic acid | 0% | 0% | 1% | 0% | 0% | 0% |
| 4-Hydroxybenzenesulphonic acid | 0% | 0% | 0% | 1% | 0% | 0% |
| 2,4-Dihydroxybenzoic acid | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 1 | 2 | 2 | 2 | 4 |
| Frizz | 4 | 2 | 1 | 2 | 2 | 3 |
| Clean Feel | 4 | 4 | 3 | 4 | 4 | 1 |

Results of Hair Switch Rating from Class I Molecules:
Molecules (5-chlorosalicylic acid, salicylic acid, 4-hydroxybenzenesulphonic acid, 2,4-dihydroxybenzoic acid) from Class I provide hair benefits. More specifically, Table 3 shows that hair treatments with 5-chlorosalicyclic acid, salicylic acid, 4-hydroxybenzenesulfonic acid and 2,4-dihydroxybenzoic acid provide frizz protection with clean feel and without greasy feel negative, as opposed to treatment with terminal aminosilicone, which provide some frizz benefit but with greasy feel negative and significantly less clean feel.

TABLE 4

Aqueous compositions containing Class II Moisture Control Materials

| Raw Material | Control | Formula Example | | | | |
|---|---|---|---|---|---|---|
| | | XIX | XX | XXI | XXII | XXIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| Isostearyl isostearate | 0% | 1% | 0% | 0% | 0% | 0% |
| 2-Hydroxyethyl salicylate | 0% | 0% | 1% | 0% | 0% | 0% |
| Octyl salicylate | 0% | 0% | 0% | 1% | 0% | 0% |
| 2-Hexyl-1-decanol | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 2 | 2 | 2 | 3 | 4 |
| Frizz | 4 | 2 | 2 | 1 | 1 | 3 |
| Clean Feel | 4 | 3 | 3 | 3 | 3 | 1 |

Results of Hair Switch Rating from Class II Molecules:
Molecules (Isostearyl isostearate, 2-hydroxylethyl salicylate, octyl salicylate, 2-hexyl-1-decanol) from Class II provide hair benefits. More specifically, Table 4 shows that hair treatment with isostearyl isostearate, 2-hydroxyethyl salicylate, octyl salicylate, and 3-hexyl-1-decanol provide frizz protection with clean feel and without greasy feel negative, as opposed to treatment with terminal aminosilicone, which provide some frizz benefit but with greasy feel negative and significantly less clean feel.

Evaluation of Hair Friction

Leave-on formulation containing Moisture Control Material and Silicone oil shows improvement in dry feel compared to untreated hair. This is concluded by measurement of dry hair friction. For this evaluation, natural virgin brown hair switches (4.0 g) are washed with clarifying shampoo, and then treated with leave-on treatment of composition XXIV according to the protocol described above. Before the evaluation, the switches are air dried overnight in a controlled temperature and humidity room (22° C./50% RH). The friction force (grams) between the hair surface and a urethane pad along the hair is measured, with three measurements per switch using an Instron Tester instrument (Instron 5542, Instron, Inc, Canton, Mass., USA).

TABLE 5

Hair Friction

| Raw Material | Formula Example | Control Hair - No Treatment |
|---|---|---|
| | XXIV | |
| Distilled Water | 49.5% | |
| Ethanol | 49.5% | |
| 2,4 dihydroxybenzoic acid | 1% | |
| Silicone oil | 0% | |
| Composition pH adjusted to | 4.2 | |
| Average Force (g) | 40 | 55 |

As Table 5 indicates, treatment of hair with leave-on composition containing Moisture Control material and silicone oil results in reduced hair friction, which indicates improved dry feel.

It is known that organic hydrophobic molecules that are naturally present inside the hair (e.g. as part of Cell Membrane Complex lipids) contribute to its strength and integrity. It is also known that cosmetic treatments, such as oxidative coloring and permanent shaping result in reduction of the concentration of such hydrophobic material from hair. Thus, penetration of hydrophobic materials (e.g. Class II materials) inside the hair can contribute to lipid replenishment, which, at the same time, reduces water uptake to deliver moisture or frizz control benefit. Combination of different Class II materials e.g. benzyl alcohol, 2-hexyl-1-decanol, isostearyl isostearate, have multi-functionality of penetration, getting embedded into lipid of hair and also increasing the penetration of other hydrophobic materials like oleic resulting in further increase hydrophobicity of the hair interior.

pH of Aqueous Compositions

In an embodiment of the present invention, the table below demonstrates data of the difference of % water reduction of hair treated with leave on composition containing 1% salicylic acid in ethanol:water (50:50) at various values of pH vs control (hair treated with composition of ethanol:water (50:50). As shown in below table, at lower pH, the present invention demonstrates improved performance compared to higher pH.

TABLE 6

Impact of pH on efficacy of moisture control materials in aqueous formulation

| | Formula Example | | | |
|---|---|---|---|---|
| Raw Material | pH 3 | pH 4.2 | pH 7 | pH 10 |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Water Reduction | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the pH of a composition of the present invention comprising materials from Molecular Class II may be in the range of from about 1 to about 9, in another embodiment a pH of from about 2 to about 8, and in a further embodiment a pH of from about 3 to about 7.

TABLE 7

Non-aqueous Leave-on Treatment Compositions:

| | | Formula Example | | | | |
|---|---|---|---|---|---|---|
| Raw Material | Control (wt./wt.)% | A (wt./wt.)% | B (wt./wt.)% | C (wt./wt.)% | D (wt./wt.)% | E (wt./wt.)% |
| Dimethicone | 20 | 20 | 20 | 20 | 20 | 20 |
| Cyclopentasiloxane | QS | QS | QS | QS | QS | QS |
| Isododecane | 0 | | | | | |
| Salicylic acid | 0 | 1 | | | | |
| 2,4 dihydroxybenzoic acid | 0 | | 0.15 | | | |
| 2-hexyldecanol | 0 | | | 5 | | |
| Isostearyl Isostearate | 0 | | | | 2 | |
| Propylene glycol | <=20 | 10 | | | | 10 |
| Viscosity (mPas) at 20 deg C. | — | <=20 | <=20 | <=20 | <=20 | <=20 |
| % Water Reduction versus Leave-on Treatment Control at dose of 0.10 g of composition for 1.0 g of hair | 4 | 1.9 | 0.2 | 1 | 0.4 | 0.3 |
| Frizz Rating versus Leave-on Treatment Control at dose of 0.10 g of composition for 1.0 g of hair (on scale of 5, Highest frizzy hair (/worst frizz control) is 5 and Lowest frizzy hair (/best frizz control) is 1) | | 2 | 3 | 3 | 3 | 4 |

TABLE 8

Non-aqueous Leave-on Treatment Compositions

| | | Formula Example | | | | |
|---|---|---|---|---|---|---|
| Raw Material | Control (wt./wt.)% | F (wt./wt.)% | G (wt./wt.)% | H (wt./wt.)% | I (wt./wt.)% | J (wt./wt.)% |
| Dimethicone | 20 | 20 | 20 | 45 | 45 | 90 |
| Cyclopentasiloxane | QS | QS | QS | QS | | QS |
| Isododecane | | | | | QS | |
| Salicylic acid | | 1 | 1 | 1 | 1 | 1 |
| 2,4 dihydroxybenzoic acid | | 0.15 | 0.15 | 0.15 | 0.15 | 0.15 |
| 2-hexyldecanol | | 5 | 5 | 5 | 5 | 5 |
| Isostearyl Isostearate | | 2 | 2 | 2 | 2 | 2 |
| Propylene glycol | | 10 | 10 | 10 | 10 | 10 |
| Viscosity (mPas) at 20 deg C. | <=20 | <=20 | <=20 | 250-300 | 250-300 | 1500-2500 |
| % Water Reduction versus Leave-on Treatment Control at dose of 0.10 g of composition for 1.0 g of hair | | 2.7 | 3 | 1.9 | 1.8 | 3.2 |

TABLE 8-continued

Non-aqueous Leave-on Treatment Compositions

| | Formula Example | | | | | |
|---|---|---|---|---|---|---|
| Raw Material | Control (wt./wt.)% | F (wt./wt.)% | G (wt./wt.)% | H (wt./wt.)% | I (wt./wt.)% | J (wt./wt.)% |
| Frizz Rating versus Leave-on Treatment Control at dose of 0.10 g of composition for 1.0 g of hair (on scale of 5, Highest frizzy hair (/worst frizz control) is 5 and Lowest frizzy hair (/best frizz control) is 1) | 4 | 1 | 1 | 3 | 2 | 1 |

Results:

Formula A-D & F-M showed % water reduction at high humidity.

The frizz assessment results indicate that combination of Salicylic acid and 2-hexyl-1-decanol and isostearyl isostearate and 2,4 dihydroxy benzoic acid provide water absorption reduction (resulting in frizz benefit) This is shown by the frizz rating comparisons of Examples A to J Additional Evaluations Additional non-aqueous leave-on treatments compositions are prepared (Tables 9 and 10) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, smooth feel and greasy feel, based on a 5 point scale, 5 being the highest and 1 being the lowest rating.

TABLE 9

Class I Compounds in Non-aqueous Leave-on Treatment Compositions:

| | Formula Example | | | |
|---|---|---|---|---|
| Raw Material | Control | K | L | M |
| 5-Chlorosalicylic acid | 0% | 1% | 0% | 0% |
| Salicylic acid | 0% | 0% | 1% | 0% |
| 2,4-Dihydroxybenzoic acid | 0% | 0% | 0% | 1% |
| Greasy Feel | 2 | 2 | 2 | 2 |
| Frizz | 4 | 2 | 1 | 1 |
| Clean Feel | 3 | 3 | 3 | 3 |
| Smooth Feel | 4 | 4 | 4 | 4 |

Results of Hair Switch Rating from Class I Molecules:

Molecules (5-chlorosalicylic acid, salicylic acid, 4-hydroxybenzenesulphonic acid, 2,4-dihydroxybenzoic acid) from Class I provide hair benefits. More specifically, Table 9 shows that hair treatments with 5-chlorosalicyclic acid, salicylic acid, 4-hydroxybenzenesulfonic acid and 2,4-dihydroxybenzoic acid provide frizz protection with clean and smooth feel and without greasy feel negative, as opposed to treatment with terminal aminosilicone, which provide some frizz benefit but with greasy feel negative and significantly less clean feel.

TABLE 10

Class II Compounds in Non-aqueous Leave-on Treatment Compositions:

| | Formula Example | | | |
|---|---|---|---|---|
| Raw Material | Control | XIV | XV | XVI |
| Dimethiconol | 20.0% | 20% | 20% | 20% |
| Cyclopentasiloxane | 50.0% | 49.5% | 49.5% | 49.5% |
| Isostearyl isostearate | 0% | 1% | 0% | 0% |
| 2-Hydroxyethyl salicylate | 0% | 0% | 1% | 0% |
| 2-hexyl-1-decanol | 0% | 0% | 0% | 1% |
| Greasy Feel | 2 | 2 | 2 | 2 |
| Frizz | 4 | 2 | 2 | 1 |
| Clean Feel | 4 | 3 | 3 | 3 |
| Smooth feel | 4 | 5 | 5 | 4 |

Results of Hair Switch Rating from Class II Molecules:

Molecules (Isostearyl isostearate, 2-hydroxylethyl salicylate, 2-hexyl-1-decanol) from Class II provide hair benefits. More specifically, Table 10 shows that hair treatment with isostearyl isostearate, 2-hydroxyethyl salicylate, and 3-hexyl-1-decanol provide frizz protection with clean, smooth feel and without greasy feel negative, as opposed to treatment with terminal aminosilicone, which provide some frizz benefit but with greasy feel negative and significantly less clean feel.

Comparative Examples of Aqueous and Non-Aqueous Leave on Compositions,

Similar trend in efficacy of moisture control materials in aqueous and non-aqueous leave-on formulations using % water reduction from DVS is observed. This indicates that moisture control materials efficacy is independent of leave-on formulation composition.

TABLE 11

Comparative examples of Aqueous and Non-Aqueous Leave on Compositions

| Non-Aqueous Leave on Formulation Examples (% water reduction vs control at 0.1 g of leave on treatment per g of hair) | Aqueous Leave on Formulation Examples (% water reduction vs control at 0.1 g of leave on treatment per g of hair) |
|---|---|
| Formula A (1.9%) | Formula VIII (2.3%) |
| Formula C (1%) | Formula X (1%) |
| Formula D (0.4%) | Formula IX (0.7%) |

TABLE 12

In-use feel and stability comparison of aqueous and non-aqueous leave-on formulations

| Ingredients | Example 1 Weight % | Example 2 Weight % | Example 3 Weight % | Example 4 Weight % |
|---|---|---|---|---|
| Distilled Water | 50 | 50 | 0 | 0 |
| Ethanol | 50 | 25 | 0 | 0 |
| Cyclopentasiloxane | 0 | 0 | 20 | 20 |
| Dimethiconol | 0 | 0 | Q.S. | Q.S. |
| Salicylic acid | 0 | 5 | 0 | 5 |
| Isostearyl Isostearate | 5 | 5 | 0 | 5 |
| Propylene Glycol | 0 | 0 | 5 | 25 |
| In-use feel rating of leave-on formulation of application to hair, (0.1 of leave on treatment per g of hair: on scale of 5, 5 being the best feel in-use feel) | 3 | 3 | 5 | 5 |
| Visual Assessment of leave on formulation after 1 day kept at 40 deg C., 50% RH | Oil droplets | Precipitate | Clear Solution | Clear Solution |
| Visual Assessment of leave on formulation after 1 week kept at 40 deg C., 50% RH | Oil droplets | Precipitate | Clear Solution | Clear Solution |

Non-Aqueous Leave on formulation containing Moisture Control Material and Silicone oil (example 3 and 4) are rated higher in-use feel than shows improvement in-use feel compared to aqueous formulations (example 1 and 2). It is also observed non-aqueous formulation with high concentration of moisture control materials is relatively more stable on 1 day and 1 week stability check at 40 deg C. than aqueous leave-on formulations.

TABLE 13

Anhydrous Compositions in Soild Form

| Ingredients | Example 5 Weight % | Example 6 Weight % | Example 7 Weight % |
|---|---|---|---|
| Dimethicone[1] | 66 | 67 | 67 |
| Polyethylene wax[2] | 25 | 25 | 25 |
| Phenyl Trimethicone | 5 | 5 | 5 |
| Stearamidopropyl dimethylamine | 2 | 2 | 2 |
| Salicylic acid | 1 | 0 | 1 |
| Isostearyl Isostearate | 1 | 1 | 0 |

[1]Silicone oil with viscosity of 10 cSt
[2]Performalene 1290 supplied by Baker Hughes Thickener In one embodiment, the non-aqueous leave-on hair care composition comprises a thickener to increase the substantivity and stability as well as ease of use (non-dripping) of the composition. Any suitable thickener can be used. In an embodiment, the non-aqueous leave-on hair care composition may comprise from about 0.05% to about 10% of a thickener modifier, in a further embodiment, from about 0.1% to about 10% of a thickener, in yet a further embodiment, from about 0.5% to about 2% of a thickener, in a further embodiment, from about 0.7% to about 2% of a thickener, and in a further embodiment from about 1% to about 1.5% of a thickener. Nonlimited examples of such thickeners are modified silicas, fumed silicas, organoclays, waxes (hydrocarbon, silicone, fluoro-substituted, fatty acid esters), hydrophobically modified polysaccharides, hydrophobically modified polyurethanes or mixtures thereof.

The composition may also comprise at least one thickener. Nonlimited examples of such thickeners are modified silicas, fumed silicas, organoclays, waxes (hydrocarbon, silicone, fluoro-substituted, fatty acid esters), hydrophobically modified polysaccharides, hydrophobically modified polyurethanes or mixtures thereof.

Carrier

The composition contains volatile or non-volatile, linear or branched hydrocarbon liquids or mixtures thereof. Non-limited examples include mineral oil, dodecane, isododecane, squalane, cholesterol, hydrogenated polyisobutylene, docosane, hexadecane, isohexadecane, other isoparaffins or mixtures, The composition may comprise other volatile or non-volatile hydrophobic materials such as esters, ethers, carboxylic acids, esters, silicone oils, fatty alcohols, fatty amides In a further embodiment, the solvents may be dermatologically acceptable. In another embodiment, organic and silicone solvents that have boiling points below or equal to 250° C. may be volatile solvents and volatile carriers. In one embodiment, solvents with boiling points above 250° C. may be considered non-volatile.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2 d ed., pp 204-308, John Wiley & Sons, Inc. (1989), incorporated herein by reference.

Organic Conditioning Materials

The conditioning agent of the compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Hair Health Actives

In an embodiment of the present invention, a scalp health active may be added to provide scalp benefits. This group of materials is varied and provides a wide range of benefits including anti-dandruff, anti-fungal, anti-microbial, miniaturization, barrier improvement, and anti-oxidant, anti-itch, and sensates. Such skin health actives include but are not limited to: zinc pyrithione, climbazole, octopirox, vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, isocyclomone, benzyl alcohol, and natural extracts/oils including peppermint, spearmint, argan, jojoba and aloe.

Anti-Dandruff Actives

In an embodiment of the present invention, the compositions may contain anti-dandruff agents. When present in these compositions, the anti-dandruff agent is typically included in an amount of about 0.01 wt. % to about 5 wt. %, based on the total weight of the personal care composition. In these compositions, the anti-dandruff particulate should be physically and chemically compatible with other ingredients of the composition, and should not otherwise unduly impair product stability, aesthetics, or performance.

Anti-dandruff agents suitable for use in personal care compositions include pyridinethione salts, azoles (e.g., ketoconazole, econazole, and elubiol), selenium sulfide, particulate sulfur, salicylic acid, and mixtures thereof. A typical anti-dandruff agent is pyridinethione salt. Personal care compositions can also include a zinc-containing layered material. An example of a zinc-containing layered material can include zinc carbonate materials. Of these, zinc carbonate and pyridinethione salts (particularly zinc pyridinethione or "ZPT") are common in the composition, and often present together.

In addition to the anti-dandruff active, compositions may also include one or more anti-fungal or anti-microbial actives in addition to the metal pyrithione salt actives. Suitable anti-microbial actives include coal tar, sulfur, charcoal, whitfield's ointment, castellani's paint, aluminum chloride, gentian violet, octopirox (piroctone olamine), ciclopirox olamine, undecylenic acid and it's metal salts, US 2011/0305778 A1 Dec. 15, 2011 potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

i. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01 wt. % to about 5 wt. %, typically from about 0.1 wt. % to about 3 wt. %, and commonly from about 0.3 wt. % to about 2 wt. %, based on the total weight of the personal care product. Especially common for use herein is ketoconazole.

ii. Selenium Sulfide

Selenium sulfide is a particulate anti-dandruff agent suitable for use in anti-microbial personal care compositions, effective concentrations of which range from about 0.1 wt. % to about 4 wt. %, based on the total weight of the personal care product, typically from about 0.3 wt. % to about 2.5 wt. %, commonly from about 0.5 wt. % to about 1.5 wt. %. Selenium sulfide is generally regarded as a compound having one mole of selenium and two moles of sulfur, although it may also be a cyclic structure that conforms to the general formula Se$_x$S$_y$, wherein $x+y=8$. Average particle diameters for the selenium sulfide are typically less than 15 μm, as measured by forward laser light scattering device (e.g. Malvern 3600 instrument), typically less than 10 μm. Selenium sulfide compounds are described, for example, in U.S. Pat. Nos. 2,694,668; 3,152,046; 4,089,945; and 4,885,107.

iii. Sulfur

Sulfur may also be used as a particulate anti-microbial/anti-dandruff agent in anti-microbial personal care compositions. Effective concentrations of the particulate sulfur are typically from about 1 wt. % to about 4 wt. %, based on the total weight of the personal care product, typically from about 2 wt. % to about 4 wt. %.

iv. Keratolytic Agents

In some embodiments, the personal care composition can further include one or more keratolytic agents such as salicylic acid. The personal care composition may also include a combination of anti-microbial actives. Such combinations may include octopirox and zinc pyrithione, pine tar and sulfur combinations, salicylic acid and zinc pyrithione combinations, salicylic acid and elubiol combinations, zinc pyrithione and elubiol combinations, octopirox and climbazole combinations, and salicylic acid and octopirox combinations and mixtures thereof.

II. Zinc-Containing Material, Including Zinc Carbonate

In an embodiment of the present invention, compositions may include a zinc-containing layered material. Those compositions can include about 0.001 wt. % to about 10 wt. % of the zinc-containing layered material based on the total weight of the personal care composition. In an embodiment of the present invention, a personal care composition can include a zinc-containing layered material from about 0.01 wt. % to about 7 wt. % based on the total weight of the personal care composition. In yet a further embodiment of the present invention, a personal care composition can include a zinc-containing layered material from about 0.1 wt. % to about 5 wt. %, based on the total weight of the composition. Suitable zinc-containing layered materials include those described below, including zinc carbonate materials, which are presently preferred:

Zinc-containing layered structures are those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975) Zinc-containing layered materials (ZLM's) may have zinc incorporated in the layers and/or be components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLM's, which are often, but not always, synthetic, is layered doubly hydroxides, which are generally represented by the formula $[M^{2+}_{1-y}M^{3+}_x(OH)_2]^{x+}A^{m-}_{x/m} \cdot nH_2O$ and some or all of the divalent ions ($M^{2+}$) would be represented as zinc ions (Crepaldi, E L, Pava, P C, Tronto, J, Valim, J B J. Colloid Interfac. Sci. 2002, 248, 429-42).

Yet another class of ZLM's can be prepared called hydroxy double salts (Morioka, H., Tagaya, H., Karasu, M, Kadokawa, J, Chiba, K Inorg. Chem. 1999, 38, 4211-6). Hydroxy double salts can be represented by the general formula $[M^{2+}_{1-x}M^{2+}_{1+x}(OH)_{3(1-y)}]^+A^{n-}_{(1=3y)/n} \cdot nH_2O$ where the two metal ion may be different; if they are the same and represented by zinc, the formula simplifies to $[Zn_{1+x}(OH)_2]^{2x+}2xA^- \cdot nH_2O$. This latter formula represents (where x=0.4) common materials such as zinc hydroxychloride and zinc hydroxynitrate. These are related to hydrozincite as well wherein a divalent anion replace the monovalent anion. These materials can also be formed in situ in a composition or in or during a production process.

These classes of ZLM's represent relatively common examples of the general category and are not intended to be limiting as to the broader scope of materials which fit this definition.

Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union US 2011/0305778 A1 Dec. 15, 2011 Ld Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also maybe referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice Anti-dandruff efficacy can be dramatically increased in topical compositions by the combination of an anti-dandruff agent with an effective amount of a zinc-containing layered material, wherein the zinc-containing layered material has a specified zinc lability within a surfactant system. Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Labile zinc is maintained by choice of an effective zinc-containing layered material or formation of an effective zinc-containing layered material in-situ by known methods.

Anti-dandruff efficacy can be dramatically increased in topical compositions by the use of polyvalent metal salts of pyrithione, such as zinc pyrithione, in combination with zinc-containing layered materials. Therefore, personal care compositions can include those containing both anti-dandruff agents and zinc-containing layered materials for topical application to provide improved benefits to the skin and scalp (e.g., improved antidandruff efficacy).

Optional Ingredients

The compositions of the present invention can also additionally comprise any suitable optional ingredients as desired. For example, the composition can optionally include other active or inactive ingredients.

The compositions may include other common hair ingredients such as other anti-dandruff actives, minoxidil, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, *eucalyptus* oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, and any other form that may be applied to the hair.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A non-aqueous, leave-on composition for hair frizz reduction comprising:
   from about 0.15% to about 12.0% of a moisture control material or mixture of moisture control materials wherein the moisture control material is selected from one or more of the following class:
   1) Class II having the structure selected from:

a)

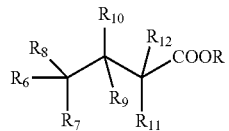

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

b)

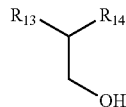

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
   c) an alcohol comprising an unsaturated double bond in the C2 position;
   d) an alkyl-substituted glycol wherein the structure of such alkyl substituted glycol contains less than 20 carbon atoms;
   e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

f)

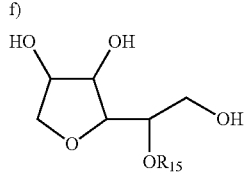

wherein $R_{15}$ could be hydrogen, alkyl, alkenyl, phenyl group and wherein the structure of the $R_{13}$ group contain less than 20 carbon atoms;
   g) a fatty acid ester containing from 15-40 total carbon atoms;
   and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4,
   and wherein, the non-aqueous, leave-on composition further comprises a non-aqueous carrier is selected from a group consisting of
   i. hydrocarbons;
   ii. silicone fluid;
   iii. non-hydrocarbons volatile organic solvents, or mixtures thereof, and further comprising salicylic acid in combination with one or more compounds of the group consisting of isostearyl isostearate, 2-hexyl-1-decanol, and propylene glycol.

2. A non-aqueous hair leave-on composition according to claim 1 wherein the concentration of the moisture control material or the concentration of the mixture of moisture control material is from about 0.2% to about 5%.

3. A non-aqueous hair leave-on composition according to claim 1 wherein the concentration of the moisture control material or the concentration of the mixture of moisture control material is from about 0.5% to about 4%.

4. A non-aqueous hair leave-on composition according to claim 1 wherein the concentration of the moisture control material or the concentration of the mixture of moisture control material is from about 1.02% to about 3.0%.

5. A non-aqueous hair leave-on composition according to claim 1 wherein the non-aqueous, leave-on composition further comprises a weakly polar to non-polar, weakly to non-acidic material is selected from the group consisting of isovaleric acid, isobutyric acid, 2-hexydecanol, phytol, sorbitan caprylate, vitamin E succinate, glyceryl monooleate, isostearyl isostearate, ethyl linoleate, isopropyl myristate, 3-aminophenol, 3-hydroxyanilinium chloride, 2-aminophenol, 4-aminophenol, Bis[(4-hydroxyphenyl)ammonium] sulphate, N-4-hydroxyphenyl glycine, and mixtures thereof.

6. A non-aqueous hair leave-on composition according to claim 5 wherein the moisture control material is 2-hexyl-1-decanol.

7. A non-aqueous hair leave-on composition according to claim 1 wherein the moisture control material is an ester in Class II, and wherein the moisture control material has a % Protein binding (PB) >20 AND Molecular Volume (Mol. Vol.) <500 AND Partition coefficient octanol to water (log P)<3 AND Hydrogen binding (H-binding) >10.

8. A non-aqueous hair leave-on composition according to claim 1 further comprising salicylic acid in combination with one or more compounds of the group consisting of isostearyl isostearate, 2-hexyl-1-decanol, glyceryl monooleate, benzyl alcohol and propylene glycol.

9. A non-aqueous hair leave-on composition according to claim 1 further comprising salicylic acid in combination with 2-hexyl-1-decanol and isostearyl isostearate.

10. A non-aqueous hair leave-on composition according to claim 1 further comprising salicylic acid in combination with 2-hexyl-1-decanol.

11. A non-aqueous hair leave-on composition according to claim 1 further comprising salicylic acid in combination with isostearyl isostearate.

12. A non-aqueous hair leave-on composition according to claim 1 further comprising salicylic acid in combination with 2,4-dihydrobenzoic acid, 2-hexyl-1-decanol and oleic acid.

13. A non-aqueous hair leave-on composition according to claim 1 further comprising 5-chlorosalicylic acid in combination with 2-hexyl-1-decanol and oleic acid.

14. A non-aqueous hair leave-on composition according to claim 1 wherein the composition further comprises propylene glycol.

15. A non-aqueous hair leave-on composition according to claim 1 wherein the composition further comprises silicone.

16. A non-aqueous hair leave-on composition according to claim 1 comprising a mixture methyl palmitate and methyl stearate.

17. A non-aqueous hair leave-on composition according to claim 1 comprising the product of the reaction between refined palm kernel oil and methanol.

18. A non-aqueous hair leave-on composition according to claim 1 wherein the composition further comprises materials selected from the group consisting of conditioning materials, solvents, rheology modifier, thickeners, hair health actives, anti-dandruff actives, anti-oxidants, pigments, abrasives, absorbents, biological actives, chelating agents, opacifying agents and mixtures thereof.

19. A non-aqueous hair leave-on composition according to claim 18 wherein the composition further comprises a metal salt of pyrithione.

20. A non-aqueous hair leave-on composition wherein the silicone of claim 1 is a volatile silicone.

21. A non-aqueous hair leave-on composition according to claim 1 comprising a mixture of dimethicone/dimethiconol and cyclopentasiloxane/isododecane.

22. A non-aqueous hair leave-on composition wherein the hydrocarbon of claim 1 is selected from isododecane, and C8-20 isoparaffins.

23. A non-aqueous hair leave-on composition according to claim 1 wherein the volatile organic solvent is isododecane.

24. A non-aqueous hair leave-on composition according to claim 1 wherein the composition comprises salicylic acid in combination with a hydrocarbon and silicone.

25. A non-aqueous hair leave-on composition according to claim 1 wherein the physical state of the composition is a solid form.

26. A non-aqueous hair leave on composition of claim 25 wherein the carrier comprises of a wax.

27. A non-aqueous hair leave on composition of claim 26 wherein a wax is polyethylene wax.

28. A non-aqueous hair leave on composition of claim 26 wherein the composition further comprises a silicone fluid.

29. A non-aqueous hair leave on composition of claim 28 wherein the composition further comprises a cationic surfactant.

30. A non-aqueous hair leave on composition of claim 29 wherein the cationic surfactant is stearamidopropyl dimethylamine (SAPDMA).

31. A non-aqueous hair leave on composition of claim 28 wherein the composition further comprises phenyltrimethicone.

32. A non-aqueous hair leave on composition of claim 21 wherein the composition comprises salicylic acid and isostearate isostearate.

33. A hair treatment application delivery system comprising the non-aqueous leave-on composition of claim 1 wherein a hair treatment application delivery system comprises a clip, brush, comb, roller, glove, wipe, stick, or a multi-piece applicator device.

* * * * *